United States Patent [19]
Koppel et al.

[11] 3,987,121
[45] Oct. 19, 1976

[54] PROCESS FOR SEPARATING ALPHA-PINENE FROM BETA-PINENE

[75] Inventors: Paul Martin Koppel, Springfield; William I. Taylor, Summit, both of N.J.

[73] Assignee: International Flavors & Fragrances Inc., New York, N.Y.

[22] Filed: Aug. 26, 1975

[21] Appl. No.: 607,998

[52] U.S. Cl. .............................. 260/675.5; 203/64
[51] Int. Cl.[2] ..................... C07C 13/42; C07C 7/06; B01D 3/36
[58] Field of Search ..................... 260/675.5; 203/64

[56] References Cited
UNITED STATES PATENTS

| | | | |
|---|---|---|---|
| 3,278,623 | 10/1966 | Derfer | 260/675.5 |
| 3,310,478 | 3/1967 | Amir | 203/64 X |
| 3,655,803 | 4/1972 | Miller | 260/675.5 |

*Primary Examiner*—Delbert E. Gantz
*Assistant Examiner*—G. E. Schmitkons
*Attorney, Agent, or Firm*—Arthur L. Liberman; Franklin D. Wolffe

[57] ABSTRACT

A process for effecting at least the partial resolution of a first pinene mixture containing alpha pinene and beta pinene is described comprising the sequential steps of (i) admixing diethylene glycol with said first pinene mixture of alpha pinene and beta pinene thus forming a second pinene mixture; (ii) subjecting the resulting second pinene mixture of alpha pinene, beta pinene and diethylene glycol to fractional azeotropic distillation yielding (A) a distillate which is a two liquid phase non-emulsified composition the first phase of which is the lower phase and which consists essentially of diethylene glycol and the second phase of which is the upper phase and which consists essentially of a third pinene mixture consisting essentially of alpha pinene and beta pinene, substantially richer in alpha pinene than said first pinene mixture and (B) a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said first pinene mixture; and (iii) physically separating said first phase from said second phase by means of decantation.

A preferred manner of carrying out such process comprises the sequential steps of (i) first removing, in the absence of azeotroping agent, by means of distillation a portion of the α-pinene from the first pinene mixture whereby 80% of the α-pinene is removed from the first pinene mixture of α-pinene and beta pinene and whereby said first pinene mixture is enriched in concentration of beta pinene, thereby forming a second pinene mixture; (ii) admixing diethylene glycol with the resulting second pinene mixture of alpha pinene and beta pinene to form a third pinene mixture; (iii) subjecting the resulting third pinene mixture of alpha pinene, beta pinene and diethylene glycol to fractional azeotropic distillation yielding (A) a distillate which is a two liquid phase non-emulsified composition; the first phase of which is a lower phase and which consists essentially of diethylene glycol and the second phase of which is the upper phase and which consists essentially of a fourth pinene mixture consisting essentially of alpha pinene and beta pinene substantially richer in alpha pinene than said second pinene mixture and (B) a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said first pinene mixture; and (iv) physically separating said first phase from said second phase by decantation.

6 Claims, 5 Drawing Figures

α-PINENE AND β-PINENE VAPOR-LIQUID EQUILIBRIUM WITH ENTRAINER

○ = WITH DIETHYLENE GLYCOL ENTRAINER (30 % OF PINENE)

FIG. 1 BATCH DISTILLATION WITH DIETHYLENE GLYCOL

FIG. 2 CONTINUOUS DESTILLATION WITH DIETHYLENE GLYCOL

FIG. 4

PROCESS FOR SEPARATING ALPHA-PINENE FROM BETA-PINENE

BACKGROUND OF THE INVENTION

This invention relates to the resolution of alpha and beta pinene mixtures and particularly to the treatment of terpene fractions containing alpha and beta pinene.

Customarily, naturally-occurring beta pinene has been isolated from certain alpha pinene-rich turpentines, e.g. gum and sulfate turpentine. Beta-pinene is useful as a raw material for producing terpene resins and Nopol (6,6-dimethyl bicyclo (3,1,1)-2-heptene-2-ethanol) regardless of its optical configuration, and is particularly valuable as a raw material in the synthesis of fine chemicals such as 1-menthol and dl-citronellol when such pinene has high optical activity (laevo rotation).

Alpha pinene is much more abundant and has been less valuable as a starting material for chemical synthesis, when compared with beta pinene. Mixtures of alpha pinene and beta pinene rich in beta pinene are obtainable by means well known in the art, for example according to the process taught in U.S. Pat. No. 3,278,623 issued on Oct. 11, 1966 which process comprises establishing contact between a supply of a mixture of alpha-pinene and beta-pinene and a transitory hydrogen acceptor catalyst which is one or more of the elements of Group VIII having an atomic number between 28 and 78 or palladium chloride or platinum oxide under neutral to basic conditions in a reaction zone maintained between room temperature and about 300° C. and withdrawing from the reaction zone mixtures richer in beta pinene.

One of the most efficient methods of recovering an ingredient from a mixture of liquid, or liquifiable ingredients is by fractional distillation. Yet so far as is known it has not heretofore been possible to recover beta pinene by distillation in a substantially pure state from mixtures of alpha pinene and beta pinene. This past inability to recover beta pinene in a highly purified state and at low cost by distillation is due to the fact that the volatility of alpha pinene relative to beta pinene is low.

Azeotropes of alpha pinene with another chemical compound are known, (e.g. ethylene glycol) as are azeotropes of beta pinene with other chemical compounds known. See Lecat, "Tables Azeotropiques"-/Tome Premier 2nd Ed/UCCLE-Bruxelles, July, 1949, Page 147. However, no azeotropes are indicated in the prior art to exist having the following properties with respect to alpha pinene and beta pinene:

1. An azeotroping chemical having a relatively low cost yet having a relatively high stability and low solubility in each of alpha pinene and beta pinene;
2. An azeotroping chemical having a boiling point (at a given pressure) greater than either of the boiling points of alpha pinene or the boiling point of beta pinene;
3. An azeotroping chemical having such physical properties whereby only small amounts of azeotrope co-distill with the beta pinene (that is, the composition of distillate product contains at most 15 mole % azeotroping agent).
4. An azeotroping chemical which allows a reduction of the number of distillation column plates or stages which are required to effect the separation required, or alternatively, and preferably, allows a reduction in the amount of reflux required in a column having the same number of plates or stages whereby a reduction in the quantity of energy required to cool the condenser and impart heat to the reboiler is effected; and
5. An azeotroping agent, the use of which in a batch distillation will permit a substantial increase in throughput (grams/hour of beta-pinene product) for the same strength of resulting beta-pinene product; and gives rise to a substantially diminished time of distillation and a lesser total quantity of energy input to the system The use of diethylene glycol as an entrainer useful in facilitating the separation of pairs of compounds is known generally in the art; but not specifically with respect to terpene compound mixture separation.

Thus U.S. Pat. No. 2,265,939 issued on Dec. 9, 1941 discloses a method of separating phenol from its mixture with cyclohexanone by adding to the mixture one of a group of compounds, including diethylene glycol, and separating phenol from the resultant mixture by distillation.

In addition, in accordance with U.S. Pat. No. 3,125,496 issued on Mar. 17, 1964 α-naphthol is stated to be recovered in a highly purified state from mixtures thereof with tetralol and tetralone by subjecting such mixtures to fractional distillation in the presence of diethylene glycol which forms an azeotropic mixture with tetralone but does not form an azeotropic mixture with α-naphthol.

U.S. Pat. No. 3,655,803 (Class 260, subclass 675.5) issued on Apr. 11, 1972, discloses a technique for producing an α-pinene product of low sulfur content by continuously fractionally distilling crude sulfate turpentine into a sulfur rich overhead distillate fraction having an α-pinene content between 2 and 20 weight percent, and a bottoms fraction of higher boiling materials, and fractionally distilling the bottoms fraction to recover product as an α-pinene distillate fraction.

THE INVENTION

This invention relates to the resolution of alpha and beta pinene mixtures and particularly to the treatment of terpene fractions containing alpha and beta pinene.

Specifically, our invention concerns a continuous or batch process for effecting at least the partial resolution of a first pinene mixture containing alpha pinene and beta pinene e.g. turpentine, which process comprises the sequential steps (batchwise, or continuous, or combination thereof) of (i) admixing diethylene glycol with said first pinene mixture of alpha pinene and beta pinene thus forming a second pinene mixture; (ii) subjecting the resulting second pinene mixture of alpha pinene, beta pinene and diethylene glycol to fractional azeotropic distillation yielding (A) a distillate which is a two liquid phase non-emulsified composition the first phase of which is the lower phase and which consists essentially of diethylene glycol and the second phase of which is the upper phase and which consists essentially of a third pinene mixture consisting essentially of alpha pinene and beta pinene, substantially richer in alpha pinene than said first pinene mixture and (B) a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said first pinene mixture; and (iii) physically separating said first phase from said second phase by means of decantation.

A preferred process of our invention for effecting such partial resolution of a first pinene mixture containing alpha pinene and beta pinene comprises the sequential steps (batchwise or continuous or a combination thereof) of (i) removing by means of distillation a portion of the alpha pinene from the first pinene mixture whereby 80% of the alpha pinene is removed from the first pinene mixture of alpha pinene and beta pinene and whereby said first pinene mixture is enriched in concentration of beta pinene, thereby forming a second pinene mixture; (ii) admixing diethylene glycol with the resulting second pinene mixture of alpha pinene and beta pinene to form a third pinene mixture; (iii) subjecting the resulting third pinene mixture of alpha pinene, beta pinene and diethylene glycol to fractional azeotropic distillation yielding (A) a distillate which is a two liquid phase non-emulsified composition; the first phase of which is a lower phase and which consists essentially of diethylene glycol and the second phase of which is the upper phase and which consists essentially of a fourth pinene mixture consisting essentially of alpha pinene and beta pinene substantially richer in alpha pinene than said second pinene mixture; and (B) a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said first pinene mixture; and (iv) physically separating said first phase from said second phase by decantation.

It is thus a principal object of this invention to provide a process by which β-pinene can be recovered in a highly purified state by fractional distillation from mixtures thereof with α-pinene. It is a more particular object of the invention to obtain highly purified β-pinene from mixtures such as turpentine. Other objects and features of the invention will be apparent from the more detailed description which follows.

In accordance with this invention, it has been found that β-pinene can be recovered in a highly purified state from mixtures thereof with α-pinene by subjecting mixtures, such as those set out above, to fractional distillation in the presence of diethylene glycol. It has been found that diethylene glycol forms an azeotropic mixture with α-pinene and with β-pinene; but it has now been discovered that diethylene glycol has the following properties with respect to alpha pinene and beta pinene:

1. Diethylene glycol is an azeotroping chemical having a relatively low cost yet having a relatively high stability and low solubility in each of alpha pinene and beta pinene;

2. Diethylene glycol is an azeotroping chemical having a boiling point (at a given pressure) greater than either of the boiling points of alpha pinene or the boiling point of beta pinene; and 3. Diethylene glycol is an azeotroping chemical having such physical properties whereby only small amounts of azeotrope co-distill with the beta pinene (that is the composition of distillate Product contains at most 15 mole % azeotroping agent).

4. Diethylene glycol is an azeotroping chemical which allows a reduction of the number of distillation column plates or stages needed to effect the required separation of α-pinene from β-pinene or, alternatively, and preferably, allows a reduction in the amount of reflux required in a distillation column having the same number of plates or stages whereby a reduction in the quantity of energy required to cool the condenser and impart heat to the reboiler is effected; and 5. Diethylene glycol is an azeotroping agent, the use of which, in a batch distillation, will permit a 50% increase in throughput (grams/hour) of beta-pinene product for the same strength of resulting beta-pinene product and, the use of diethylene glycol gives rise to a substantially diminished time of distillation and a lesser total quantity of energy input to the system. For instance, it is known that diethylene glycol boils at 165° under 40mm Hg pressure and 244° C. at 760mm Hg pressure. Yet at 760mm Hg pressure a mixture thereof with α-pinene forms an azeotrope containing 97% of α-pinene by weight with a minimum boiling point at 149.5° C. Thus the boiling point of this azeotrope is pronouncedly lower than the boiling point of pure glycol or the β-pinene (158.3° C. at 760mm Hg) and is clearly sufficient to permit a full recovery of the azeotropic mixture of diethylene glycol and α-pinene below the volatilization temperature of the β-pinene. According to our findings, the alpha-pinene and beta-pinene lower the boiling point of the diethylene glycol.

Since the azeotrope with diethylene glycol contains 97% α-pinene by weight, it has been found that diethylene glycol should be added in a quantity of from 3 up to 50% by weight of the pinene (both α-pinene and β-pinene) in order that an adequate amount thereof may be present to form the azeotroping mixture. It has been our experience that usually diethylene glycol in an amount of 30% of the total pinene mixture is adequate. Since, as stated above, diethylene glycol boils at 165° C. under 40mm Hg pressure or at 244° C at 760mm Hg pressure, it will be seen that any excess of diethylene glycol can be recovered (after removal of α-pinene) easily, either:

i. after the subsequent distillation of the beta-pinene, when starting with a turpentine mixture, by distilling (at 165° C. at 40 mm Hg pressure or at 244° C. at 760 mm Hg pressure) after distilling or after decanting turpentine heavies; or ii. without specifically distilling beta-pinene when starting with a simple mixture of α-pinene and β-pinene, by decantation of the 2-phase mixture; or iii. when starting with turpentine and taking a β-pinene-diethylene glycol vapor sidestream from the distillation column, then separating condensate by decantation of the diethylene glycol lower phase.

Figure 1:
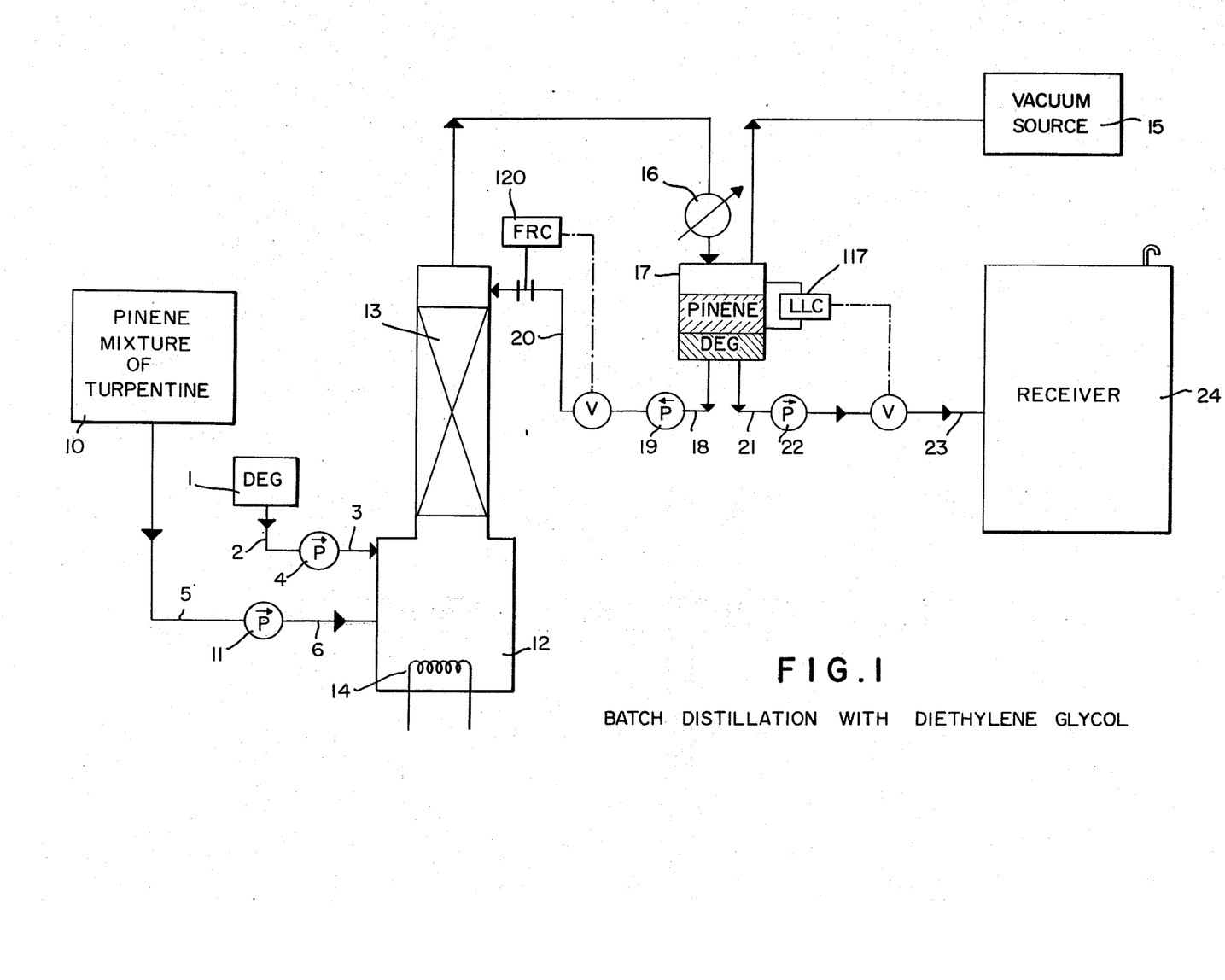
FIG. 1 illustrates apparatus useful in carrying out a batch azeotropic distillation for separating α-pinene from β-pinene using a diethylene glycol azeotroping agent. Turpentine, analyzed as follows.
Figure 2:
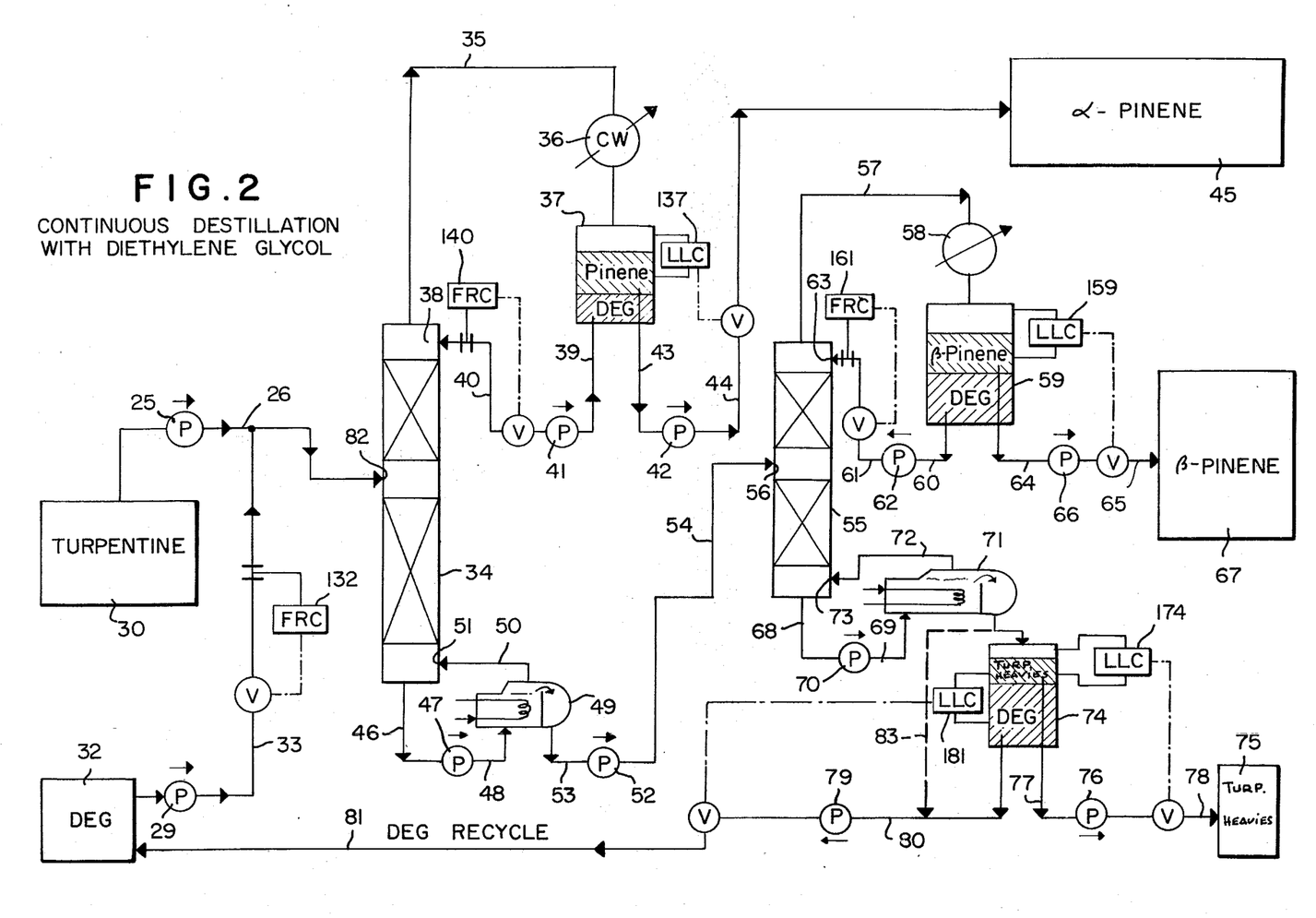
FIG. 2 illustrates apparatus useful in carrying out a continuous azeotropic distillation for separating alpha-pinene from beta-pinene using a diethylene glycol azeotroping agent. Turpentine, analyzed as follows.
Figure 5:
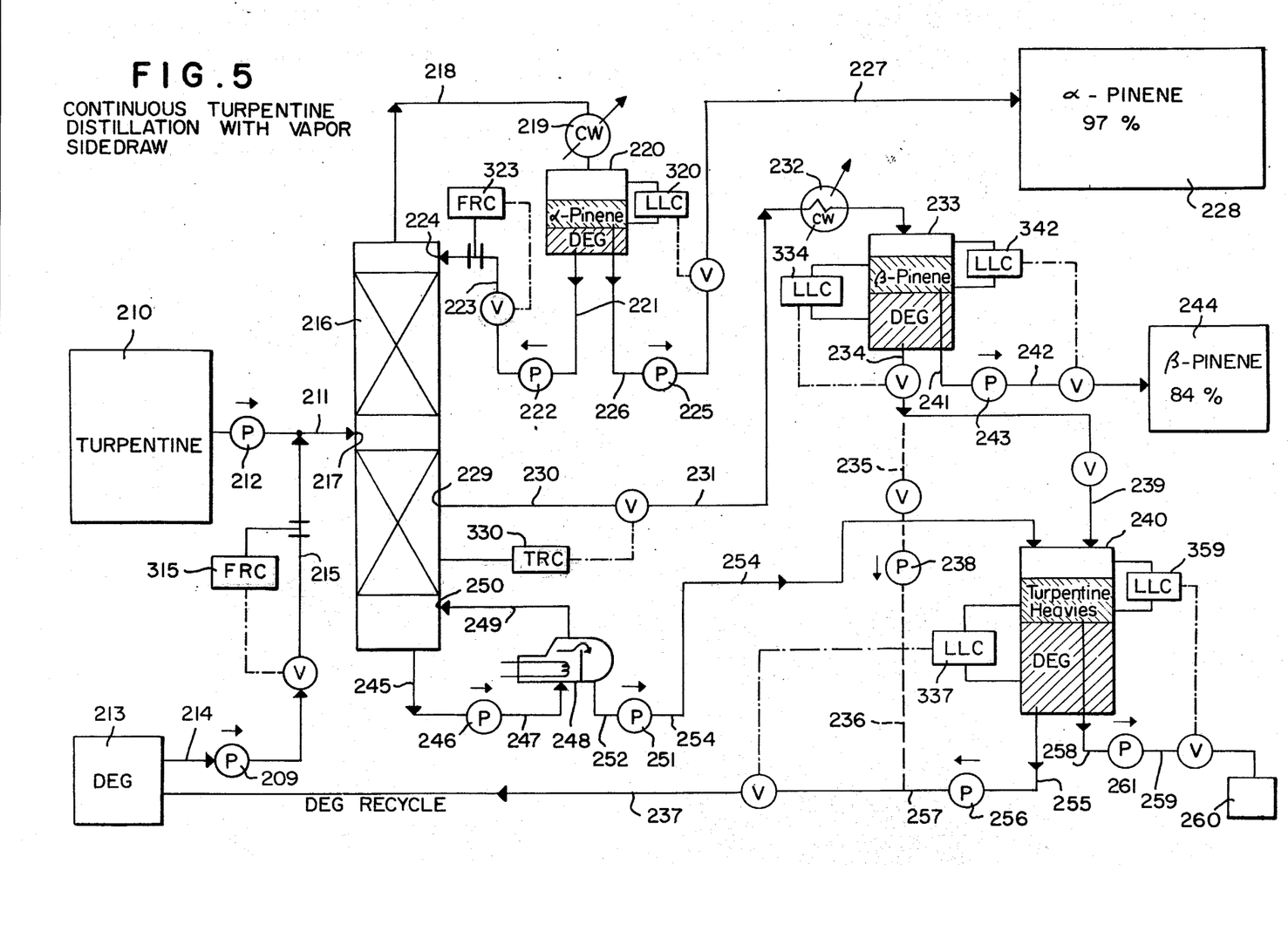
FIG. 5 illustrates apparatus including but one distillation column with a vapor "side draw" or "sidestream" useful in carrying out a continuous azeotropic distillation for separating alpha-pinene, beta-pinene and turpentine heavies from one another using a diethylene glycol azeotroping agent. Turpentine, analyzed as follows.

FIGS. 1, 2 and 5 illustrate these techniques in detail.

Diethylene glycol, due to its ready availability, and inexpensiveness, constitutes a preferred substance having functional groups creating an azeotropic mixture with α-pinene and β-pinene and having a volatility pronouncedly different from the almost ideal mixture formed by alpha-pinene with β-pinene thereby permitting the separation of β-pinene from such mixture in a highly purified form.

The invention will further be understood by reference to (1) the examples which set forth purely illustrative processes for the batchwise and continuous distillation column recovery of beta-pinene in a highly purified state from azeotropic mixtures using diethylene glycol as an entrainer and (2) to the drawings and reference thereto.

EXAMPLE I

A. Into a 5 liter flask equipped with heating mantle, stirrer, thermometer and 2 feet × 60 mm Goodloe column (apparatus according to FIG. 1) the following materials are placed:

| Ingredient | Quantity (gm) |
| --- | --- |
| Turpentine | 3000 |
| Diethylene Glycol | 600 |

Heat is applied to the contents of the flask causing the resulting mixture to distill and yielding the following alternative bulkings containing the indicated mole percentages of beta-pinene:

| Bulking No. | Yield of β-Pinene based on weight of Turpentine charged | Strength of β-Pinene in Distillate |
| --- | --- | --- |
| 1 | 6.9% | 92.9% |
| 2 | 13.4 | 90.0 |
| 3 | 20.6 | 81.8 |
| 4 | 25.4 | 78.0 |

The Goodloe column contains packing produced and marketed by the Packed Column Co., Division of Metex Corporation of 970 New Durham Road, Edison, N.J. 08817 and is described in their brochure entitled: "Packed Column Information Bulletin/How to Design a Goodloe Column."

B. Into a 5 liter flask equipped with heating mantle, stirrer, thermometer and 2 feet × 60 mm Goodloe Column (apparatus according to FIG. 1) is placed 3000 gm Turpentine, (and no entrainer). Heat is applied to the contents of the flask causing the resulting mixture to distill and yielding the following alternative bulkings containing indicated mole percentages of beta-pinene:

| Bulking No. | Yield of β-Pinene based on weight of Turpentine charged | Strength of β-Pinene in Distillate |
| --- | --- | --- |
| 1 | 5.1 | 90.7 |
| 2 | 11.4 | 88.3 |
| 3 | 17.8 | 76.4 |

Figure 3:
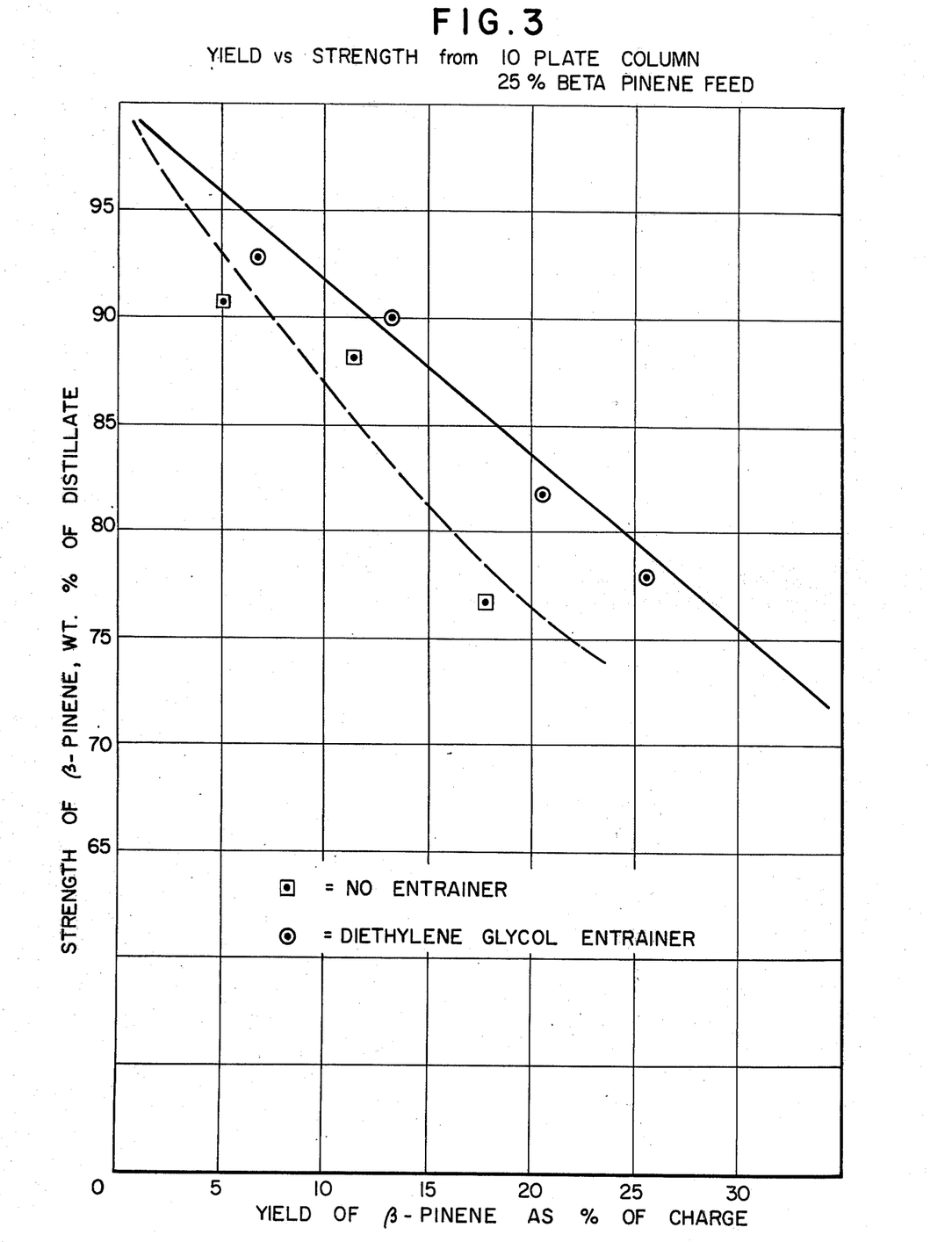
FIG. 3 is a graph on which are plotted two curves setting forth strength of beta-pinene (%) in distillate (plotted along the y-axis or ordinate or vertical axis) versus yield of beta-pinene based upon charge of turpentine to a 10 plate distillation column (plotted along the x axis or abscissa or horizontal axis); a first curve wherein diethylene glycol is used as an azeotroping agent and a second curve wherein no azeotroping agent is used (marked, respectively "curve 1" and "curve 2").

FIG. 3 sets forth two curves of % beta pinene in distillate versus yield of beta pinene as a percentage of Turpentine charge to the distillation column; a first curve wherein diethylene glycol is used as an azeotroping agent and a second curve wherein no azeotroping agent is used.

EXAMPLE II

A. Into six different 500 cc vapor-liquid equilibrium stills each of which is equipped with a thermometer, total condenser and recycle line conducting the condensate back to the heated section of the still & equipped with sampling devices for vapor condensate & pot liquid, the following materials are placed:

| Ingredient | Quantity (gm) |
| --- | --- |
| Mixture of alpha pinene and beta pinene as indicated in Table I | 120 |
| Diethylene Glycol | 34 |

Heat is applied to the contents of each of the six flasks causing each of the six resulting mixtures to distill, condense and recycle back into the pot until vapor-liquid equilibrium is achieved. At this point, a sample of the vapor condensate and a sample of the liquid in the pot are taken and analyzed. From the data, relative volatilities are calculated and shown in Table I.

TABLE I

| Mixture No. | Weight Ratio of α-pinene: β-pinene in Feed | Vapor Temp. °C | Liquid Temp. °C | Weight Ratio of α-pinene: β-pinene in- | | Relative Volatility |
| --- | --- | --- | --- | --- | --- | --- |
| | | | | Distillate | Pot | |
| No. 1 | 90:10 | 153 | 155 | 92.5:7.5 | 90.3:9.7 | 1.32 |
| No. 2 | 80:20 | 153 | 155 | 83.5:16.4 | 80:20* | 1.27* |
| No. 3 | 60:40 | 155 | 157 | 66.3:33.7 | 59.2:40.8 | 1.36 |
| No. 4 | 45:55 | 158 | 160 | 50.5:49.5 | 42.2:57.8 | 1.40 |
| No. 5 | 30:70 | 159 | 161 | 34.6:65.4 | 27.7:72.3 | 1.38 |
| No. 6 | 15:85 | 160 | 162 | 19.6:80.3 | 14.4:85.6 | 1.45 |

*Estimated

B. Into five different 500 cc vapor-liquid equilibrium stills, each of which is equipped with a heating section, thermometer, total condenser and recycle line to conduct the condensate back to the heated section of the still & equipped with sampling divices for vapor and liquid, are placed, respectively, five different mixtures of alpha pinene and beta pinene, total weighing 240g as set forth in Table II.

Heat is applied to each of the contents of the five flasks causing each of the five resulting mixtures to distill, condense, and recycle back into the pot until vapor-liquid equilibrium is achieved. At this point a sample of the vapor condensate and liquid in the pot is taken and analyzed. From this data relative volatilities are calculated and shown in Table II.

TABLE II

| Mixture No. | Weight Ratio of α-pinene: β-pinene in Feed | Vapor Temp. °C | Liquid Temp. °C | Weight Ratio of α-pinene: β-pinene in- | | Relative Volatility |
| --- | --- | --- | --- | --- | --- | --- |
| | | | | Distillate | Pot | |
| No. 1 | 90:10 | 154 | 155 | 91.4:8.6 | 88.1:11.9 | 1.44 |
| No. 2 | 80:20 | 154 | 155 | 82.8:17.2 | 77.5:22.2 | 1.38 |
| No. 3 | 45:55 | 156 | 158 | 52.4:47.6 | 44.2:55.8 | 1.39 |

TABLE II-continued

| Mixture No. | Weight Ratio of α-pinene: β-pinene in Feed | Vapor Temp. °C | Liquid Temp. °C | Weight Ratio of α-pinene: β-pinene in- Distillate | Pot | Relative Volatility |
|---|---|---|---|---|---|---|
| No. 4 | 30:70 | 158 | 159 | 35.1:64.9 | 28.8:71.2 | 1.34 |
| No. 5 | 15:85 | 157 | 160 | 19.9:80.0 | 14.5:85.5 | 1.46 |

Figure 4:
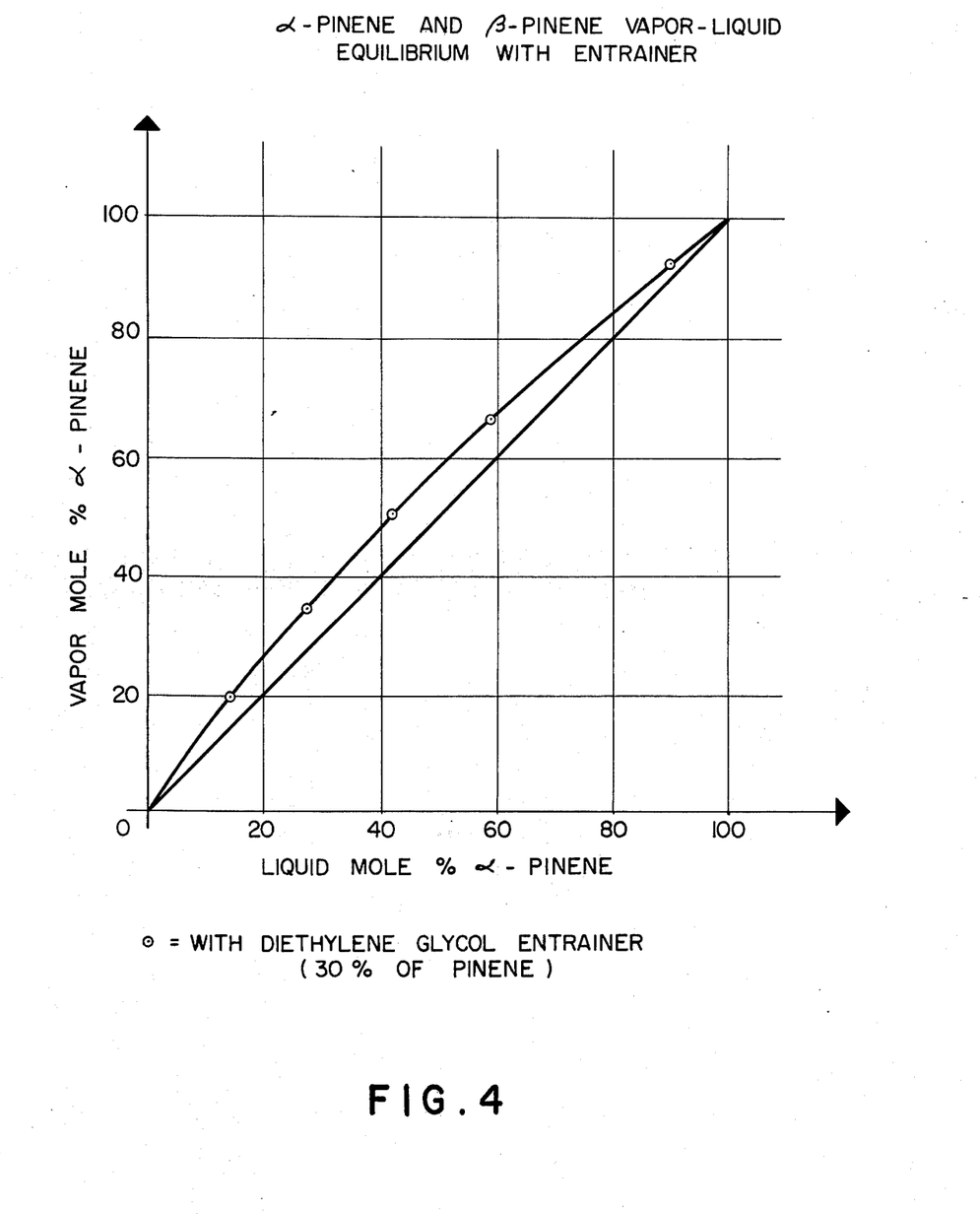
FIG. 4 is a graph which sets forth a curve showing mole percent alpha-pinene in the vapor phase (plotted along the y axis or ordinate or vertical axis) in equilibrium with mole percent alpha-pinene in the liquid phase (plotted along the x axis or abscissa or horizontal axis), wherein diethylene glycol is used as an azeotroping agent in an amount of 30% based on the weight of alpha-pinene and beta-pinene.

FIG. 4 sets forth a curve of % alpha-pinene and beta-pinene in vapor phase in equilibrium with % alpha-pinene and beta-pinene in liquid phase wherein diethylene glycol is used as an azeotroping agent.

DETAILED DESCRIPTION OF THE DRAWINGS

| Component | Weight % | Relative Retention Time Based on Alpha-pinene (Determined by GLC Analysis) |
|---|---|---|
| "Lights" | 0.8 | 0.2 |
| Alpha-Pinene | 57.2 | 1.0 |
| Camphene | 1.6 | 1.24 |
| Beta-Pinene | 25.5 | 1.61 |
| "Heavy I" | 1.9 | 1.96 |
| "Heavy II" | 6.4 | 2.23 |
| "Heavy III" | 0.7 | 2.50 |
| "Extra Heavy I" | 1.1 | 3.5–4.1 |
| "Extra Heavy II" | 1.2 | 4.4 |
| "Extra Heavy III" | 1.3 | 4.6 |
| "Extra Heavy IV" | 1.0 | 4.8 |
| "Extra Heavy V" | 1.3 | 4.9–5.5 | or a mixture of alpha-pinene and beta-pinene is charged through lines 5 and 6 using pump 11, from storage vessel 10 into vessel 12 to which multistage distillation column 13 is fitted. Either: (a) Diethylene glycol is initially charged from holding tank 1, through lines 2 and 3 using pump 4 prior to the distillation or (b) Diethylene glycol is charged at some time subsequent to the commencement of the distillation (optimum: after 80% of the alpha-pinene is removed from the charge by means of distillation). The distillation is carried out by application of heat at 14 and, if and as desired, vacuum at 15. At first, the material distilling over is rich in α-pinene. On condensation in the cooling heat exchanger 16 the distillate then exists in two phases; an upper phase consisting of α-pinene and β-pinene which is rich in α-pinene and a lower phase consisting of diethylene glycol; and this distillate is collected in separator 17. The lower phase, consisting primarily of diethylene glycol is recycled together with some upper phase pinene (at a rate to provide the desired reflux, controlled by flow recorder controller 120 [also designated in the drawing by the letters "FRC"]) through lines lines 18 and 20 by means of pump 19 into the distillation column 13. The upper phase is removed from the separator (at a rate controlled by liquid level controller 117 [also designated in the drawing by the letters "LLC"]) using pump 22, through lines 21 and 23 into receiver 24. As this batch distillation proceeds, the upper phase of distillate mixture becomes richer in β-pinene and the last one-third of the distillate (boiling lower than the "heavy fractions" normally not distilled in that case where the batch charged is turpentine) consists of mixtures of α-pinene and β-pinene containing greater than 80% β-pinene.

As a result of operating the process of our invention using the apparatus of FIG. 1 a significant cycle time reduction is effected as a result of the (batch fractionation of turpentine in a 30–35 stage column (8 ft. × 3 in. Goodloe column)) use of a diethylene glycol entrainer and this is illustrated in the following Table III:

TABLE III

| | Without Diethylene Glycol | With Diethylene Glycol | |
|---|---|---|---|
| | | Experiment A EQUAL YIELD | Experiment B EQUAL STRENGTH PRODUCT |
| Turpentine Charge Weight, gms. | 15000. | 15000. | 15000. |
| Diethylene Glycol Charge Weight, gms. | 0. | 3000. | 3000. |
| Operating Pressure, mm Hg | 760. | 760. | 760. |
| Maximum Reflux Ratio | 29/1 | 29/1 | 29/1 |
| Yield Product, Weight % Charge | 27. | 27. | 24.5 |
| Strength Product, Weight % beta-pinene | 93. | 89. | 93. |
| Beta-Pinene Contained in Product, gms. | 3766. | 3604. | 3418. |
| Batch Cycle Time, Hrs. | 49. | 29. | 29. |
| Beta-Pinene Throughput, gms./hr. | 77. | 124. | 118. |
| Increase in Throughput, % | — | 61. | 53. |

| Component | Weight % | Relative Retention Time Based on Alpha-Pinene (Determined by GLC Analysis) |
|---|---|---|
| "Lights" | 0.8 | 0.2 |
| Alpha-Pinene | 57.2 | 1.0 |
| Camphene | 1.6 | 1.24 |
| Beta-Pinene | 25.5 | 1.61 |
| "Heavy I" | 1.9 | 1.96 |
| "Heavy II" | 6.4 | 2.23 |

-continued

| Component | Weight % | Relative Retention Time Based on Alpha-Pinene (Determined by GLC Analysis) |
|---|---|---|
| "Heavy III" | 0.7 | 2.50 |
| "Extra Heavy I" | 1.1 | 3.5–4.1 |
| "Extra Heavy II" | 1.2 | 4.4 |
| "Extra Heavy III" | 1.3 | 4.6 |
| "Extra Heavy IV" | 1.0 | 4.8 |
| "Extra Heavy V" | 1.3 | 4.9–5.5 | or a mixture of alpha-pinene and beta-pinene is pumped (using pump 25) from storage vessel 30 through lines 26 and 31 while diethylene glycol is pumped (using pump 20), at a rate controlled by flow recorder controller 132, from storage vessel 32 through lines 33 and 31 into a multistage distillation column 34. The overhead distillate composition, richer in α-pinene than the feed, passes through line 35 and is condensed, in cooling heat exchanger 36, the two liquid phase condensate being collected in separator 37. The lower phase, consisting primarily of diethylene glycol is recycled together with some upper phase pinene (at a rate to provide the desired reflux, controlled by flow controller 140) into the distillation column 34 at 38 through lines 39 and 40 using pump 41. The upper phase, a mixture of α-pinene and β-pinene, rich in α-pinene is removed (at a rate controlled by liquid level controller 137) using pump 42 through lines 43 and 44 into receiver 45. the bottoms from the distillation passes through line 46 and is pumped with pump 47 through line 48 into reboiler 49. A light fraction portion of the bottoms is vaporized in the reboiler and passes through line 50 into the distillation column 34 at 51. The remainder of the bottoms, consisting of β-pinene, diethylene glycol and, when such materials as turpentine are used, heavy components of said turpentine, is pumped using pump 52 through lines 53 and 54 into distillation column 55 operated at partial reflux, at 56. The distillate rich in β-pinene, passes through line 57 and is condensed in cooling heat exchanger 58. The condensate is collected in separator 59. On condensation, the distillate exists in two different phases: a lower phase consisting of β-pinene and diethylene glycol, and an upper phase consisting of -pinene in concentration of greater than 90%. The lower phase of this condensate and some upper phase is recycled at a rate controlled by FRC 161 through lines 60 and 61 using pump 62 into the distillation column 55 at 63. The remaining β-pinene-rich upper phase is removed at a rate controlled by LLC 159 from the separator using pump 66, through lines 64 and 65 into receiver 67. The bottoms from the distillation operation carried out in column 55 is pumped through lines 68 and 69 using pump 70 into reboiler 71. A light fraction is vaporized from reboiler 71 and returned through line 72 into distillation column 55 at 73. The non-volatile heavy fraction from the reboiler exists in two phases in the event that the charge from 30 is turpentine; or a diethylene glycol rich single phase in the event that the charge from 30 is a simple mixture of α-pinene and β-pinne. In the event that the charge from 30 is turpentine, then the two resulting non volatile liquid phases are separated in separator 74. The upper phase, consisting of turpentine "Heavy" components is pumped (at a rate controlled by liquid level controller 174) into receiver 75 using pump 76 through lines 77 and 78. The lower phase, consisting of diethylene glycol is recycled (at a rate controlled by liquid level controller 181), using pump 79 through lines 80 and 81, back into the diethylene glycol storage vessel 32. In the event that the charge from 30 is simply a mixture of alpha-pinene and beta-pinene, then the resulting non volatile liquid consisting of diethylene glycol is recycled using pump 79 through lines 83, 80 and 81 into diethylene glycol storage vessel 32.

| Component | Weight % | Relative Retention Time Based on Alpha-Pinene (Determined by GLC Analysis) |
|---|---|---|
| "Lights" | 0.8 | 0.2 |
| Alpha-Pinene | 57.2 | 1.0 |
| Camphene | 1.6 | 1.24 |
| Beta-Pinene | 25.5 | 1.61 |
| "Heavy I" | 1.9 | 1.96 |
| "Heavy II" | 6.4 | 2.23 |
| "Heavy III" | 0.7 | 2.50 |
| "Extra Heavy I" | 1.1 | 3.5–4.1 |
| "Extra Heavy II" | 1.2 | 4.4 |
| "Extra Heavy III" | 1.3 | 4.6 |
| "Extra Heavy IV" | 1.0 | 4.8 |
| "Extra Heavy V" | 1.3 | 4.9–5.5 | is pumped from storage vessel 210 through line 211 using pump 212 while diethylene glycol is pumped using pump 209 (at a rate controlled by flow recorder controller 315) from storage vessel 213 through lines 214, 215 and 211 into distillation column 216 at 217, at the 17th stage (from the top) of the distillation column. The distillation column 216 is 100 feet in packed height and 40 inches in diameter, and packed with Koch Flexirings; and is determined to have 50 stages (2 feet per stage). The overhead distillate composition, richer in alpha-pinene than the feed, passes through line 218 and is condensed, in cooling heat exchanger 219, the two-liquid phase condensate being collected in separator 220. The lower phase, consisting primarily of diethylene glycol is recycled together with some upper phase pinene (at a rate to provide the desired reflux controlled by flow recorder controller 323) into the distillation column 216 at 224 through lines 221 and 223 using pump 222. The upper phase, a mixture of alpha-pinene and beta-pinene, rich in alpha-pinene is removed (at a rate controlled by liquid level controller 320) using pump 225 through lines 226 and 227 into receiver 228. A vapor sidestream containing diethylene glycol and beta-pinene is removed from distillation column 216 at 229 (from the 36th stage of the distillation column as measured from the top of the column) through lines 230 and 231 at a rate controlled by temperature recorder controller 330 [also designated in the drawing by the letters "TRC"]. The vapor sidestream is condensed in cooling heat exchanger 232. On condensation, the distillate exists in two different phases: a lower phase consisting primarily of diethylene glycol, and an upper phase consisting of beta-pinene in a concentration of greater than 84%. The condensate is collected in separator 233 at a rate controlled by LLC 334. The lower phase of this condensate is either (i) recycled through lines 234, 235, 236 and 237, using pump 238 into diethylene glycol storage vessel 213; or (ii) passed into separator 240 through lines 234 and 239, where it becomes a part of the lower phase of two liquid phases contained therein. The upper phase of the condensate collected in separator 233 is pumped through lines 241 and 242, using pump 243, at a rate controlled by liquid level controller 342 into receiver 244. The bottoms from the distillation passes through line 245 and is pumped with pump 246 through line 247 into reboiler 248. A light fraction portion of the bottoms is vaporized in the reboiler and passes through line 249 into the distillation column 216 at 250. The remainder of the bottoms, consisting of two phases; diethylene glycol and heavy components of turpentine, is pumped using pump 251 through lines 252 and 254 into separator 240. The lower phase of this composition together with, optionally, lower phase from separator 233 recycled through lines 255, 257 and 237, using pump 256 into the diethylene glycol storage vessel 213 at a rate controlled by flow recorder controller 337. The upper phase in separator 240 consisting of turpentine "Heavy" components is pumped (at a rate controlled by liquid level controller 359) into receiver 260 using pump 261 through lines 258 and 259.

A material balance around the system illustrated in FIG. 5 is as follows:

| STREAM | RATE LBS/HR | COMPOSITION, WT. % | | | | TEMP. °C. |
| --- | --- | --- | --- | --- | --- | --- |
| | | ALPHA-PINENE | CAMPHENE | BETA-PINENE | HEAVIES | |
| 1. Distillate | 1080. | 97.0 | 2.1 | 0.8 | .001 | 156. |
| 2. Vapor Sidedraw | 500. | 4.8 | 1.5 | 83.8 | 9.9 | 175. |
| 3. Bottoms | 275. | .03 | .03 | 17.2 | 82.5 | 192. |
| 4. Feed | 1855. | 58. | 1.6 | 25.5 | 14.9 | Saturated Liquid |

As a result of operating the process of our invention using the apparatus of FIG. 5, the following utilities savings (using a diethylene glycol entrainer in continuous fractionation of beta-pinene from turpentine) are achieved:

TABLE IV

| | Without Diethylene Glycol | With Diethylene Glycol | Quantitative Advantage as a Result Of use of Diethylene Glycol Entrainer |
| --- | --- | --- | --- |
| Turpentine Feed Rate, Lbs./Hr. | 1855 | 1855 | — |
| Beta-Pinene Product On Rate, Lbs./Hr. | 500 | 500 | — |
| Yield (weight % of Turpentine Charge) | 27. | 27. | — |
| Strength of Product (weight % of beta-pinene) | 84. | 84. | — |
| Column Stages | 50. | 50. | — |
| Operating Pressure | 1 atm. | 1 atm. | — |
| Feed Stage (No. of stages from top of column) | 17 | 17 | — |
| Vapor Sidestream Stage (No. of stages from top of column) | 36 | 36 | — |
| % Increase in Throughput compared with process of Example 1 | — | 53. | 53% Increase in throughput |
| Reflux Ratio | 18/1 | 11.4/1 (Note 1) | 36.6% Decrease in reflux ratio |
| Vapor to Condenser, Lbs./Hr. | 20,520. | 13,392. | 34.8% Decrease in Quantity of vapor to condenser |
| Condenser Duty, BTU/Hr. | 2,210,000. | 1,440,000. | 34.8% Decrease in Condenser Duty |
| Cooling Water Required, Gals./Hr. | 8,833. | 5,768. | 35% Decrease in Cooling Water required |
| Reboiler Duty, BTU/Hr. | 2,280,000. | 1,510,000 | 33.7% Decrease in Reboiler duty |
| Steam (250 psig) | | | |

TABLE IV-continued

| | Without Diethylene Glycol | With Diethylene Glycol | Quantitative Advantage as a Result Of use of Diethylene Glycol Entrainer |
|---|---|---|---|
| required, Lbs./Hr. | 2764. | 1830 | 34% |

Note 1:
Reflux reduction allowed by increased throughput due to diethylene glycol entrainer.

What is claimed is:

1. A process for effecting at least the partial resolution of a first pinene mixture containing alpha-pinene and beta-pinene which process comprises the sequential steps of (i) admixing diethylene glycol with said first pinene mixture of alpha-pinene and beta-pinene thus forming a second pinene mixture; (ii) subjecting the resulting second pinene mixture of alpha-pinene, beta-pinene and diethylene glycol to fractional azeotropic batch distillation yielding (A) a distillate which is a two liquid phase non-emulsified composition the first phase of which is the lower phase and which consists essentially of diethylene glycol and the second phase of which is the upper phase and which consists essentially of a third pinene mixture consisting essentially of alpha-pinene and beta-pinene, substantially richer in alpha-pinene than said first pinene mixture and (B) a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said first pinene mixture; and (iii) physically separating said first phase from said second phase by means of decantation.

2. The process of claim 1 comprising the additional sequential diethylene glycol recycling step (iv) and admixing at least a portion of said first phase consisting essentially of diethylene glycol with said first pinene mixture and again carrying out, in sequence, steps (ii) and (iii).

3. The process of claim 1, operated as a continuous process.

4. A process for effecting at least the partial resolution of a first pinene mixture containing alpha pinene and beta pinene which process comprises the sequential steps of (i) removing by means of distillation a portion of the alpha pinene from the first pinene mixture whereby 80% of the alpha pinene is removed from the first pinene mixture of alpha pinene and beta pinene and whereby said first pinene mixture is enriched in concentration of beta pinene, thereby forming a second pinene mixture; (ii) admixing diethylene glycol with the resulting second pinene mixture of alpha pinene and beta pinene to form a third pinene mixture; (iii) subjecting the resulting third pinene mixture of alpha pinene, beta pinene and diethylene glycol to fractional azeotropic distillation yielding A. a distillate which is a two liquid phase non-emulsified composition; the first phase of which is a lower phase and which consists essentially of diethylene glycol and the second phase of which is the upper phase and which consists essentially of a fourth pinene mixture consisting essentially of alpha pinene and beta pinene substantially richer in alpha pinene than said second pinene mixture and B. a bottoms mixture, which is a two liquid phase, non-emulsified composition, the first phase of which is the lower phase and which consists essentially of diethylene glycol and the second phase of which is the upper phase and which consists essentially of alpha-pinene and beta-pinene substantially richer in beta-pinene than said second pinene mixture; and (iv) physically separating said first phase from said second phase by decantation.

5. The process of claim 4 comprising the additional sequential diethylene glycol recycling step (v) and admixing at least a portion of said first phase with said second pinene mixture and again carrying out, in sequence, steps (iii) and (iv).

6. The process of claim 4 operated as a continuous process.

* * * * *

UNITED STATES PATENT AND TRADEMARK OFFICE
CERTIFICATE OF CORRECTION

PATENT NO. : 3,987,121
DATED : October 19, 1976
INVENTOR(S) : PAUL MARTIN KOPPEL and WILLIAM I. TAYLOR It is certified that error appears in the above–identified patent and that said Letters Patent are hereby corrected as shown below:

Col. 11 and 12, line 53:

" — 53.        53% Increase in                    throughput"

replace it with:

" —         53.                          53% Increase in
                                              throughput"

Signed and Sealed this

Twenty-sixth Day of April 1977

[SEAL]

Attest:

RUTH C. MASON
Attesting Officer

C. MARSHALL DANN
Commissioner of Patents and Trademarks